United States Patent [19]

Mosseri et al.

[11] Patent Number: 6,093,141
[45] Date of Patent: Jul. 25, 2000

[54] STEREOTACTIC RADIOTREATMENT AND PREVENTION

[75] Inventors: Morris Mosseri; Zeev Weshler, both of Jerusalem, Israel

[73] Assignee: Hadasit Medical Research and Development Company Ltd., Jerusalem, Israel

[21] Appl. No.: 08/896,051

[22] Filed: Jul. 17, 1997

[51] Int. Cl.[7] .................................................. A61N 5/00
[52] U.S. Cl. ............................................................ 600/1
[58] Field of Search ................................. 600/1–8, 424, 600/425, 427; 378/62–65; 250/302, 303, 370.08, 370.09, 371

[56] References Cited

U.S. PATENT DOCUMENTS 3,351,049  11/1967  Lawrence .................................... 600/8
4,702,228  10/1987  Russell, Jr. et al. ........................ 600/8

OTHER PUBLICATIONS

Med. Phys. 21 (5), May 1994, pp. 643–650, Semiautomated matching and seed position location for implanted ribbons, by Kassaee andA tschuler.

Gehring et al, "A Three–Dimensional Volume Visualization Package Applied to Stereotactic Radiosurgery Treatment Planning", *Int. J. Radiation Oncology Biol. Phys.*, vol. 21, pp 491–500 (1989).

Lutz et al, "A System for Stereotactic Radiosurgury aith a Linear Accelerator", *Int. J. Radiation Oncology Biol. Phys.*, vol. 14, pp 373–381 (1987).

Schlegel et al, "Computer Systems and Mechanical Tools for Stereotactically Guided Conformation Therapy with Linear Accelerators", *Int. J. Radiation Oncology Biol. Phys.*, vol. 24, pp 781–787 (1992).

Perlovsky et al, "Multi–Sensor ATR and Identification of Friend or Foe Using MLANS", *Neural Networks*, vol. 8, No. 7/8, 1185–1200 (1995).

Zamorano et al, "Transportation of Image–defined Trajectories into Arc–quadrant Centered Stereotactic Systems", *Acta Neurochirurgica*, Suppl. 46, pp 109–111, (1989).

Hall, et al, "An Introduction to Multisensor Data Fusion", Proc. IEEE, vol. 85, No. 1, pp 6–23 (1997).

Baim, D., "Angiography: Proper Utilization of Cineangiographic Equipment and Contrast Agents", Chap. 4 of Cariac Catherization, Angiography, and Intervention, 5th Ed., Baim & Grossman, Eds., William & Wilkins, Pub.

Bauer, B., "Stereotactic Radiosurgery Treatment Planning", Nucletron–Oldelft Activity report No. 6, 1995, Nucletron Research B.V., Waardgelder 1, 3905 TH Veenendaal, The Netherlands.

*Primary Examiner*—John P. Lacyk
*Attorney, Agent, or Firm*—Mark M. Friedman

[57] ABSTRACT

A method and apparatus for dynamic stereotactic radiotreatment and prevention of restenosis. A stent is implanted in a coronary artery, following percutaneous transluminal coronary angioplasty. Subsequent restenosis is minimized by external irradiation of the stent by ionizing radiation such as gamma rays. The fact that the stent is significantly more opaque to x-rays than the surrounding tissue is exploited to track the stent using fluoroscopy, so that the ionizing radiation can be aimed accurately at the stent. Preferably, the fluoroscopic imaging and the irradiation of the stent are synchronized with the patient's cardiac cycle. The external irradiation may be performed hours or days after implanting the stent, for prevention of restenosis, or weeks or months after implanting the stent, for treatment of restenosis, and may be fractionated.

13 Claims, 2 Drawing Sheets

STEREOTACTIC RADIOTREATMENT AND PREVENTION

FIELD AND BACKGROUND OF THE INVENTION

The present invention relates to a method of prevention or treatment of restenosis by irradiation and, more particularly, to a method of treatment of restenosis by external stereotactic irradiation.

The most common therapy for ischemic heart disease is percutaneous transluminal coronary angioplasty, or "balloon" angioplasty, in which a constricted coronary artery is dilated by the insertion of a balloon. One complication of this therapy is that restenosis, or recurrent narrowing, occurs in 30%–40% of dilated arteries. To prevent this, a stent often is implanted in the dilated segment. As a foreign material, the stent induces the proliferation of smooth muscle cells in the vessel walls, so that the restenosis is not eliminated, but is only reduced to about 20%. Therefore, the implantation of the stent may be supplemented with radiotherapy, in which a radioisotope is inserted into the dilated segment or into the implanted stent in order to prevent the proliferation of the smooth muscle cells. This is time consuming, requires costly safety arrangements in the catheterization laboratory, should be performed during invasive catheterization, presents a problem of non-homogeneous irradiation of the dilated segment and adjacent segments (depending on centralization of the radioisotope) as well as different vessel wall layers, and has logistical problems because of the short half life (order of days to months), and consequent short shelf life, of the radioisotopes.

Stereotactic radiotreatment is a recognized therapy for deep seated brain tumors. See, for example, Wendell Lutz, Ken R. Winston and Nasser Maleki. "A system for stereotactic radiosurgery with a linear accelerator", Int. J Radiation Oncology Biol. Phys. Vol. 14 pp. 373–381 (1988). In this mode of therapy, beams of ionizing radiation, typically gamma radiation from a radioisotope such as $^{60}$Co or from a linear accelerator, are directed at the tumor from several angles. All the beams pass through the tumor, but each beam passes through a different portion of the tissue outside the tumor. In this way, a therapeutic dose of radiation is delivered to the tumor without damage to the surrounding tissue.

In order for stereotactic radiotreatment to succeed, the location of the target of the treatment must be known precisely, and the radiation source must be aimed precisely at the target. This is possible in the case of brain tumors, which are fixed in position relative to the patient's head, and whose location can be determined by non-invasive means, but not in the case of moving targets such as coronary arteries. Therefore, it has not been possible heretofore to treat restenosis with stereotactic radiotreatment, despite the advantages that such treatment would have over the present method of radioisotope insertion or implantation.

There is thus a widely recognized need for, and it would be highly advantageous to have, a method of stereotactic radiotreatment or prevention of restenosis.

SUMMARY OF THE INVENTION

According to the present invention there is provided a method for therapeutic treatment of a body passageway, including the steps of: (a) implanting a marker in the passageway; and (b) irradiating the marker from outside the passageway.

According to the present invention there is provided an apparatus for stereotactic radiotreatment of a moving target in a patient, including: (a) a mechanism for tracking the target; and (b) a mechanism for directing a beam of ionizing radiation at the target from outside the patient and in accordance with the tracking.

The scope of the present invention includes external irradiation of any moving target, within a patient, that can be marked by implanting, in a body passageway of the patient, a marker that can be imaged by non-invasive physical means, such as electromagnetic radiation (for example, x-rays or infrared radiation), ultrasound, or external detection of a source of low level radiation on the marker itself. The marker may be a stent, a coil, or any other foreign object; or radioactively labeled tissue. The body passageways included in the scope of the present invention include all body passageways that exhibit motion, whether periodic or irregular, rapid or slow, that prevents the application of conventional stereotactic radiotreatment. Among these body passageways are the vessels of the circulatory system, the gastrointestinal tract and the genitourinary tract. The radiation directed at the marker from outside the patient may be any suitable ionizing radiation, including gamma radiation and x-rays.

Nevertheless, the primary focus of the present invention is on the treatment or prevention of restenosis in a coronary artery. In this application, the present invention exploits the fact that the stent, being made of metal, is significantly more opaque to external irradiation such as x-rays or ultrasound than the surrounding tissue. The moving stent is tracked, using fluoroscopy, and ionizing radiation, typically gamma radiation, is aimed at the stent as the stent moves. This tracking is made easier by the fact that the motion of the stent is periodic, being determined by the cardiac cycle. According to one embodiment of the present invention, described in detail below, the irradiation is synchronized with a particular point in the cardiac cycle. According to another embodiment, the ionizing radiation is aimed at the stent as the stent moves.

The irradiation may be performed hours or days after implanting the stent, for prevention of restenosis, or weeks or months after implanting the stent, for treatment of restenosis, and may be fractionated.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method of stereotactic radiotreatment which can be used to treat moving targets within the body of a patient. Specifically, the present invention can be used to treat or prevent restenosis of coronary arteries.

The principles and operation of dynamic stereotactic radiotreatment according to the present invention may be better understood with reference to the drawings and the accompanying description.

The present invention is based on an extension to medicine of technology from the unrelated field of warfare.

Figure 1:
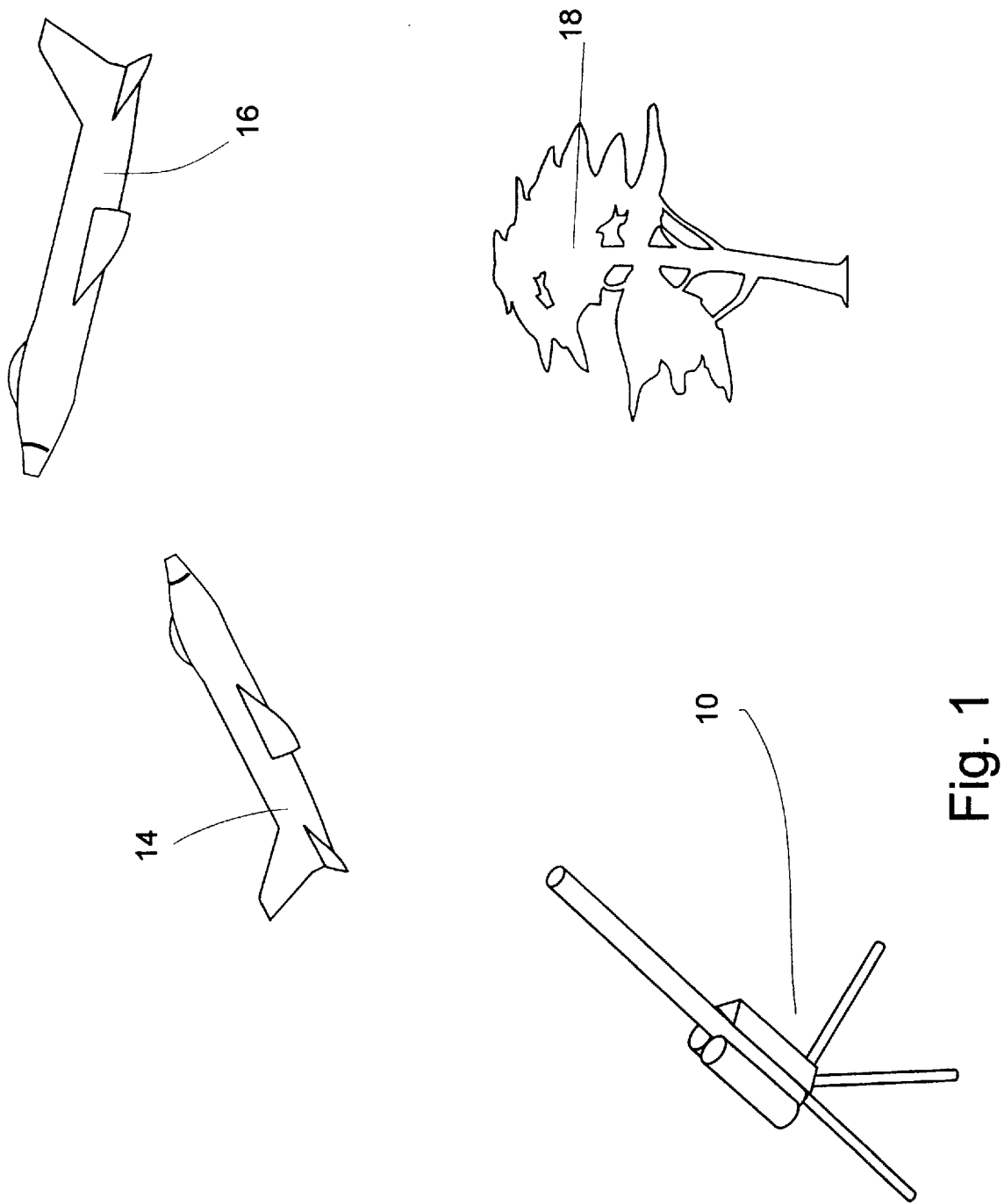
FIG. 1 is a schematic portrayal of a battlefield problem analogous to the medical problem addressed by the present invention.

Referring now to the drawings, FIG. 1 illustrates a battlefield problem that is conceptually similar to the one addressed by the present invention. It is desired to use an automatic antiaircraft gun 10 to shoot down low flying enemy aircraft 14, in the presence of friendly aircraft 16 and ground clutter 18. For this purpose, antiaircraft gun 10 is controlled by a fire control system 12. Fire control system 12 must be able to detect the presence of enemy aircraft 14, within the three-dimensional volume of the airspace above the battlefield, to distinguish enemy aircraft 14, as a proper target to be fired upon, from improper targets such as friendly aircraft 16 and ground clutter 18, to track the continuously moving enemy aircraft 14, and to aim and fire antiaircraft gun 10 at a point in space where the bullets from antiaircraft gun 10 will hit enemy aircraft 14. Methods for accomplishing this are well known. For example, enemy aircraft 14 may be identified by its radar and/or infrared signature. A variety of pattern detection algorithms can distinguish low-flying aircraft 14 from ground clutter 18. For an overview of the relevant technology, see David L. Hall and James Llinas, "An introduction to multisensor data fusion". Proc. IEEE. Vol. 85 No. 1, pp. 6–23 (January 1997). A specific example of the relevant technology that is significant in the context of the present invention is described by Leonid I. Perlovsky, Julian A. Chernick and William H. Schoendorf in "Multi-sensor ATR and Identification of Friend of Foe Using MLANS" (Neural Networks Vol. 8 No. 7/8, pp. 1185–1200, 1995). The problem addressed by Perlovsky et al. is that of automatic target recognition and tracking, and their solution is based on a neural network of MLANS architecture.

Figure 2:
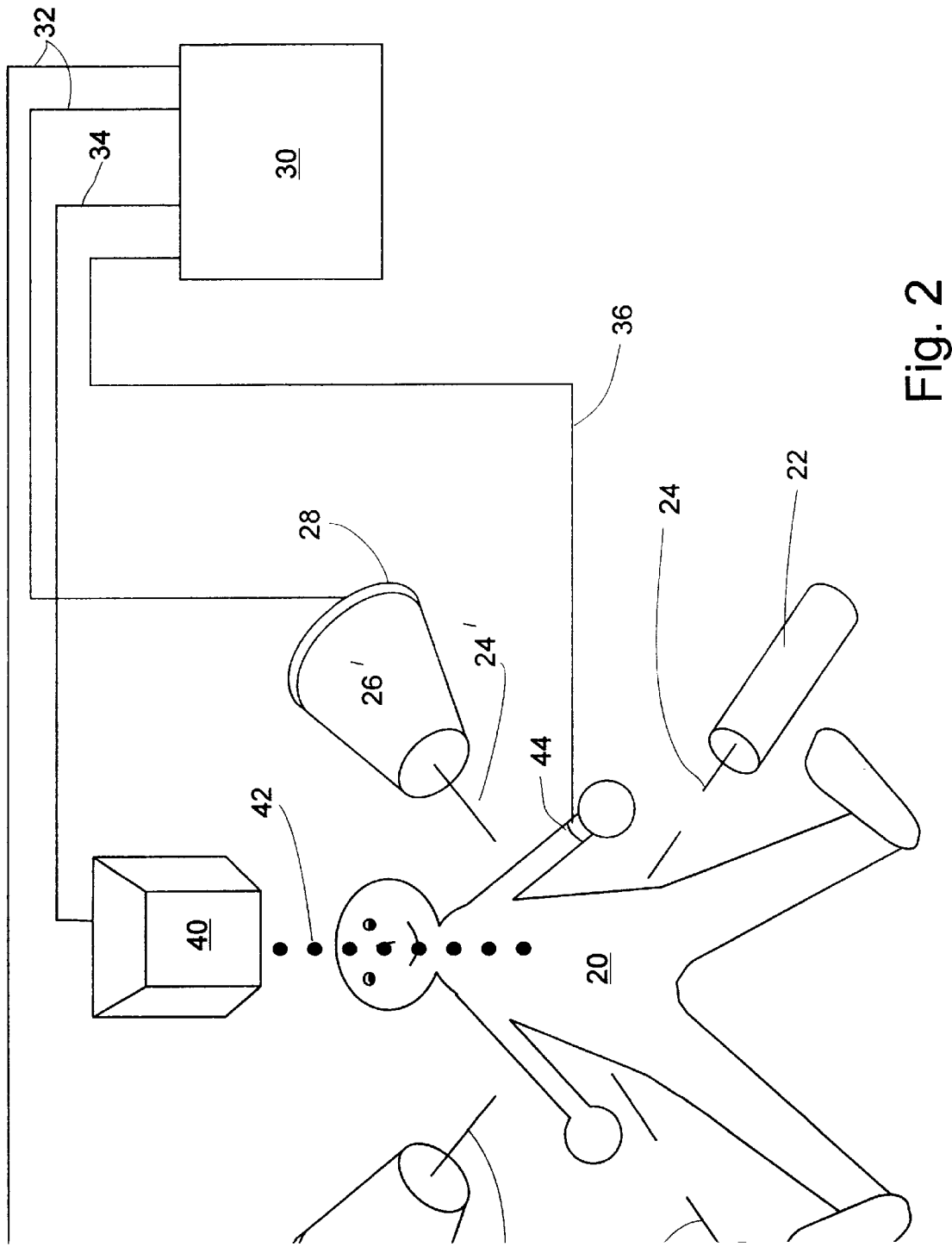
FIG. 2 is a schematic partial perspective view of an apparatus according to the present invention.

FIG. 2 illustrates an implementation of the present invention in a medical scenario that is analogous to the battlefield scenario of FIG. 1. The object is to perform stereotactic radiotherapy on a target in a patient 20, for example, a portion of a coronary artery, on the surface of the heart of patient 20, into which a stent 50 has been inserted and which is, or may in the future be, affected by restenosis. The target is analogous to enemy aircraft 14 of FIG. 1. The radiotherapy is to be performed using gamma rays 42 from a gamma ray source 40, shown in FIG. 2 directly above patient 20. Gamma ray source 40 is analogous to antiaircraft gun 10 of FIG. 1. The sensors used for target acquisition and tracking include standard fluoroscopy x-ray tubes 22 and 22' and corresponding image intensifiers 26 and 26', as described, for example, in Donald S. Baim and William Grossman, Cardiac Catheterization, Angiography, and Intervention, Williams and Wilkins, Baltimore, 1996, Chapter 4. X-ray tube 22 at the lower left of patient 20 directs an x-ray beam 24, through the chest of patient 20, that is detected by image intensifier 26 at the upper right of patient 20. X-ray tube 22' at the lower right of patient 20 directs an x-ray beam 24', through the chest of patient 20, that is detected by image intensifier 26' at the upper left of patient 20. Image intensifiers 26 and 26' are backed by charge coupled detector (CCD) arrays 28 and 28', respectively, that convert the luminescence of the output phosphors of image intensifiers 26 and 26' to electrical signals that constitute digital x-ray images of the chest of patient 20 from the two different angles defined by x-ray beams 24 and 24'. These signals are transmitted to a microprocessor-based control system 30 by conventional electrical connections 32. Control system 30 is analogous to fire control system 12 of FIG. 1.

Just as enemy aircraft 14 is identified by control system 12 from the radar and/or infrared signature of enemy aircraft 14, so the x-ray shadows of a radioopaque object such as a stent are identified by control system 30 in the images provided by CCD arrays 28 and 28' by the fact that the intensities of pixels within those shadows are considerably lower than the intensities of pixels outside those shadows. The exception is pixels corresponding to bone tissue, for example the ribs of patient 20. The stent may be more radioopaque, less radioopaque, or as radioopaque than bone tissue.

There are two ways around this problem. The first is to interactively position X-ray tubes 22 and 22', image intensifiers 26 and 26', and CCD arrays 28 and 28' so that the shadows of the stent do not overlap interfering shadows such as the shadows of ribs. The intensity distribution of the pixels in the immediate vicinity of the stent 50 then is bimodal, and it is straightforward for control system 30 to determine the intensity threshold below which a pixel corresponds to a stent. The second is to use an automatic method, such as the method of Perlovsky et al. cited above, to track the stent automatically on the basis of its properties that differ from the properties of the surrounding bone, notably that the shape and contour of the stent 50 is different from that of the surrounding bone.

With the pixels in the images corresponding to the stent 50 now identified, standard edge detection algorithms are used to define the outlines of the stent 50 in the pairs of images acquired by CCD detectors 28 and 28'. The centers of gravity of these outlines define the aiming point, in three dimensions, of gamma ray source 40. Conceptually, a line is projected, from the point on each CCD array 28 and 28' that corresponds to the center of gravity of the outline detected using that array, to the corresponding x-ray tube 22 or 22' on the other side of patient 20; and the intersection point of the two lines (or the point of closest approach, if the lines do not intersect) is the aiming point, in three dimensions, of gamma ray source 40. The fact that the stent 50 moves rhythmically and periodically with the cardiac cycle can be exploited by control system 30 to track the stent accurately in real time for the purpose of aiming gamma rays 42 thereat; but, most preferably, both the imaging using CCD arrays 28 and 28' and the irradiation using gamma ray source 40 are synchronized with a reference point in the cardiac cycle. In either case, a cardiac cycle monitor such as a pulse rate monitor 44 connected to control center 30 by conventional electrical connections 36 can be used to provide an independent measure of the timing of the cardiac cycle. Pulse rate monitor 44 is illustrative only, and the scope of the present invention includes all such monitoring methods, such as electrocardiography. Gamma ray source 40 is aimed at the aiming point from several angles, as in conventional stereotactic radiotreatment, so that the trajectories of the several beams of gamma rays 42 through patient 20 intersect only at the aiming point, thereby maximizing the dose of gamma rays absorbed at the aiming point relative to the dose absorbed by the surrounding tissue.

In order for gamma rays 42 to be aimed accurately at the stent 50, the positions and orientations of gamma ray source 40, x-ray tubes 22 and 22', image intensifiers 26 and 26' and CCD arrays 28 and 28' relative to patient 20 must be known accurately. The same prerequisite obtains for conventional stereotactic radiotherapy, in which the target is located by a 3D medical imaging technique such as CT. MRI, or PET, and the methods of positioning the diagnostic and therapeutic equipment relative to the patient that are applicable in those cases are applicable here too. See, for example, Wolfgang Schlegel, Otto Pastyr, Thomas Bortfeld, Gerd Becker, Lothar Schad, Gunther Gademann and Walter J. Lorenz, "Computer systems and mechanical tools for stereotactically guided conformation therapy with linear accelerators", Int. J Radiation Oncology Biol. Phys. Vol. 24 pp. 781–787 (1992). The principal difference between the prior art methods of stereotactic radiotherapy and the present invention is that the present invention irradiates an identifiable moving target, tracked in real time by control system 30.

As noted above, in alternative embodiments of the present invention, the imaging and the irradiation need not be synchronized with the cardiac cycle. In these embodiments, just as control system 12 aims and fires antiaircraft gun 10 at moving enemy aircraft 14, so control system 30 aims gamma rays 42 at the moving stent and irradiates the moving stent continuously.

While the invention has been described with respect to a limited number of embodiments, it will be appreciated that many variations, modifications and other applications of the invention may be made.

What is claimed is:

1. A method of therapeutic treatment of a body passageway, comprising the steps of:
    (a) implanting a marker in the passageway;
    (b) imaging the passageway, wherein the marker has been implanted, from two angles thereby providing, at each of these angles, at least one image of said marker and surrounding tissue;
    (c) identifying said marker in said images; and
    (d) irradiating said marker from outside said passageway.
2. The method of claim 1, wherein said irradiating is effected using a plurality of beams of ionizing radiation.
3. The method of claim 2, wherein said ionizing radiation is selected from the group consisting of gamma radiation and x-radiation.
4. The method of claim 1, further comprising the step of: tracking said marker.
5. The method of claim 1, wherein said imaging is effected by fluoroscopy.
6. The method of claim 1, wherein said identifying of said marker includes detecting of substantially periodic motion of said marker.
7. The method of claim 6, wherein said detecting of said substantially periodic motion includes correlating said images with an independent measure of said substantially periodic motion.
8. The method of claim 7, wherein said independent measure of said substantially periodic motion includes electrocardiography.
9. The method of claim 6, further including the step of synchronizing the radiation with said substantially periodic motion.
10. The method of claim 9, wherein said periodic motion of said marker is detected by a method selected from the group consisting of pulse monitoring and electrocardiography.
11. The method of claim 1 wherein said imaging is effected by electromagnetic radiation.
12. The method of claim 1 wherein said imaging is effected by ultrasound.
13. The method of claim 1 wherein said imaging is effected by detecting low level radiation emitted by the target.

* * * * *